US012653465B2

(12) United States Patent
Kumar et al.

(10) Patent No.: US 12,653,465 B2
(45) Date of Patent: Jun. 16, 2026

(54) PREDICTING STROKE SYMPTOMS BASED ON INTEGRATION OF VIDEO, AUDIO, AND BLOOD PRESSURE DATA

(71) Applicant: Code Blue AI, Inc., Irvine, CA (US)

(72) Inventors: Ashmita Kumar, Irvine, CA (US); Ericka Maria Corral Yanez, Denver, CO (US); Joon Beatrice Luther, San Jose, CA (US)

(73) Assignee: Code Blue AI, Inc., Irvine, CA (US)

( * ) Notice: Subject to any disclaimer, the term of this patent is extended or adjusted under 35 U.S.C. 154(b) by 0 days.

(21) Appl. No.: 19/209,101

(22) Filed: May 15, 2025

(65) Prior Publication Data

US 2025/0268539 A1      Aug. 28, 2025

Related U.S. Application Data

(63) Continuation of application No. PCT/US2024/039558, filed on Jul. 25, 2024.
(Continued)

(51) Int. Cl.
*A61B 5/00*          (2006.01)
*A61B 5/021*          (2006.01)
(Continued)

(52) U.S. Cl.
CPC .......... *A61B 5/7275* (2013.01); *A61B 5/0082* (2013.01); *A61B 5/02141* (2013.01);
(Continued)

(58) Field of Classification Search
CPC ... A61B 5/7275; A61B 5/7282; A61B 5/4803; A61B 5/7264; A61B 5/746; A61B 5/747; G16H 50/30
See application file for complete search history.

(56) References Cited

U.S. PATENT DOCUMENTS

2003/0072213 A1      4/2003   Cocoli
2014/0377727 A1 *  12/2014   Yom-Tov ............... G16H 50/20
                                                                434/236

(Continued)

OTHER PUBLICATIONS

International Search Report and Written Opinion re PCT/US24/39558 dated Oct. 21, 2024 (12 pages).

*Primary Examiner* — John R Downey
(74) *Attorney, Agent, or Firm* — Aurora Consulting LLC; Kristen J. Hansen; Ashley Sloat

(57)                    ABSTRACT

A system and method for carrying out a computer-implemented method for predicting stroke symptoms for a subject including receiving audial data representing one or more utterances of the subject; receiving image data representing one or more images of at least a portion of a face of the subject; receiving physiological data associated with the subject; predicting, based on a plurality of predefined stroke symptoms and at least two of: the audial data, the image data, and the physiological data, a likelihood of the subject is experiencing or will imminently experience one or more of the plurality of predefined stroke symptoms; in response to determining that the likelihood is above a threshold level associated with one or more of the plurality of predefined stroke symptoms, causing generation of an alert for the subject and an alert for one or more emergency contacts corresponding to the subject.

30 Claims, 5 Drawing Sheets

Related U.S. Application Data

(60) Provisional application No. 63/529,355, filed on Jul. 27, 2023.

(51) Int. Cl.

| | |
|---|---|
| *G06T 7/00* | (2017.01) |
| *G10L 25/66* | (2013.01) |
| *G16H 50/30* | (2018.01) |

(52) U.S. Cl.
CPC .......... *A61B 5/4803* (2013.01); *A61B 5/7264* (2013.01); *A61B 5/746* (2013.01); *A61B 5/747* (2013.01); *G06T 7/0012* (2013.01); *G10L 25/66* (2013.01); *G16H 50/30* (2018.01); *A61B 5/681* (2013.01); *G06T 2207/10016* (2013.01); *G06T 2207/20081* (2013.01); *G06T 2207/30004* (2013.01); *G06T 2207/30201* (2013.01)

(56) References Cited

U.S. PATENT DOCUMENTS

| | | | | |
|---|---|---|---|---|
| 2018/0153477 | A1 | 6/2018 | Nagale et al. | |
| 2018/0294060 | A1* | 10/2018 | Kassab | G16H 10/65 |
| 2019/0156944 | A1* | 5/2019 | Eriksson | G06F 18/2411 |
| 2020/0380882 | A1* | 12/2020 | Alailima | A61B 5/4836 |
| 2021/0035693 | A1* | 2/2021 | Mohammad | G16H 10/60 |
| 2022/0012634 | A1* | 1/2022 | Lee | G16H 50/20 |
| 2022/0044821 | A1* | 2/2022 | Eichler | G16H 50/20 |
| 2022/0122724 | A1* | 4/2022 | Durlach | A61B 5/447 |
| 2023/0154611 | A1* | 5/2023 | Palandurkar | G06T 7/0014 |
| | | | | 705/2 |
| 2023/0363679 | A1* | 11/2023 | Wang | G06N 3/047 |
| 2024/0115213 | A1* | 4/2024 | Ramesh | A61B 5/7282 |

* cited by examiner

400

500

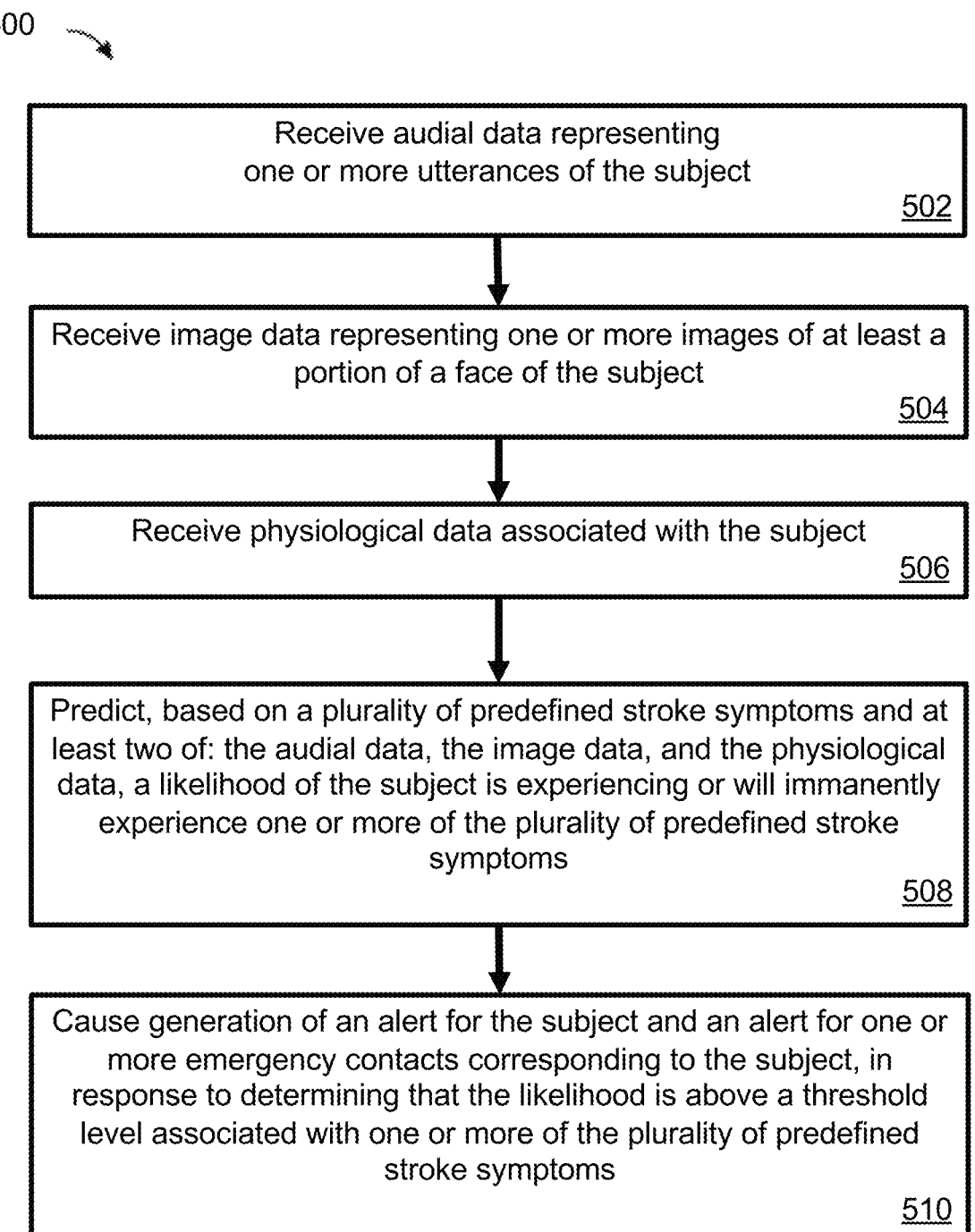

Receive audial data representing
one or more utterances of the subject

502

Receive image data representing one or more images of at least a
portion of a face of the subject

504

Receive physiological data associated with the subject

506

Predict, based on a plurality of predefined stroke symptoms and at
least two of: the audial data, the image data, and the physiological
data, a likelihood of the subject is experiencing or will immanently
experience one or more of the plurality of predefined stroke
symptoms

508

Cause generation of an alert for the subject and an alert for one or
more emergency contacts corresponding to the subject, in
response to determining that the likelihood is above a threshold
level associated with one or more of the plurality of predefined
stroke symptoms

PREDICTING STROKE SYMPTOMS BASED ON INTEGRATION OF VIDEO, AUDIO, AND BLOOD PRESSURE DATA

CROSS-REFERENCE TO RELATED APPLICATIONS

This application is continuation of International Application No. PCT/US2024/039558 filed Jul. 25, 2024, which claims the priority benefit of U.S. Provisional Application No. 63/529,355, filed on Jul. 27, 2023, the disclosures of each of which are herein incorporated by reference in their entireties.

TECHNICAL FIELD

This disclosure relates generally to the field of non-invasive detection and estimation of stroke symptoms and, more specifically, to predicting stroke symptoms based on video, audio, and/or blood pressure data.

BACKGROUND

Common signs of stroke include facial paralysis, dysarthric speech, high blood pressure, and/or arm weakness. The most common type of stroke, the ischemic stroke, occurs when a blood clot blocks oxygen and blood from flowing to the brain. After a subject experiences an ischemic stroke, the subject may suffer brain damage leading to long-term disability or death. In some situations, the damage caused by a stroke can be mitigated if detected within 30 minutes. However, individuals can generally confirm that they have experienced a stroke after the stroke event making it difficult to receive a timely diagnosis. This lack of proactive detection method leaves many individuals susceptible to the potential consequences of stroke, including paralysis, memory loss, and/or personality changes.

SUMMARY

Described herein are systems, devices, and methods related to a computer-implemented method for predicting stroke symptoms for a subject, the method including: receiving audial data representing one or more utterances of the subject; receiving image data representing one or more images of at least a portion of a face of the subject; receiving physiological data associated with the subject; predicting, based on a plurality of predefined stroke symptoms and at least two of: the audial data, the image data, and the physiological data, a likelihood of the subject is experiencing or will imminently experience one or more of the plurality of predefined stroke symptoms; and in response to determining that the likelihood is above a threshold level associated with one or more of the plurality of predefined stroke symptoms, causing generation of an alert for the subject and an alert for one or more emergency contacts corresponding to the subject.

In some aspects, the techniques described herein relate to a computer-implemented method, wherein the prediction includes accessing an ensemble learner configured to: provide the image data to a first machine learning model to generate analyzed image data for the subject; provide the audial data to a second machine learning model to generate analyzed audial data for the subject; provide the physiological data to a third machine learning model to generate analyzed physiological data for the subject; generate, based on the analyzed image data, the analyzed audial data, and the analyzed physiological data, a classifier configured to generate an indication of the subject experiencing one or more of the plurality of predefined stroke symptoms; and generating, using the classifier, a likelihood of the subject experiencing a stroke event, the likelihood being provided as output to a mobile device associated with the subject or a device associated with the one or more emergency contacts corresponding to the subject.

In some aspects, the techniques described herein relate to a computer-implemented method, wherein the prediction includes accessing an ensemble learner configured to: provide the image data to a machine learning model; receive, from the machine learning model and based on the provided image data, a risk level of the subject experiencing facial asymmetry associated with experiencing a stroke; and generate, based on the risk level, the predicted likelihood as output to a mobile device associated with the subject or a device associated with the one or more emergency contacts corresponding to the subject.

In some aspects, the techniques described herein relate to a computer-implemented method, wherein the image data includes still images or video data representing at least a portion of the face of the subject captured by the mobile device associated with the subject.

In some aspects, the techniques described herein relate to a computer-implemented method, wherein the image data is captured by a front facing camera of the device associated with the subject, the front facing camera capturing the image data during access of a video application on the mobile device associated with the subject.

In some aspects, the techniques described herein relate to a computer-implemented method, wherein the physiological data includes blood pressure data or blood oxygen data for the subject, the physiological data being captured by a wearable device in communication with a mobile device associated with the subject.

In some aspects, the techniques described herein relate to a computer-implemented method, wherein the prediction includes accessing an ensemble learner configured to: provide the audial data, the image data, and the physiological data to a machine learning model; receive, from the machine learning model and based on the provided audial data, the image data, and the physiological data, a risk level of the subject experiencing a stroke or imminently experiencing one or more of the plurality of predefined stroke symptoms.

In some aspects, the techniques described herein relate to a computer-implemented method, further including analyzing one or more of: the audial data to determine whether the audial data exhibits speech dysarthria; the image data to determine whether the image data exhibits facial asymmetry; and the physiological data to determine whether the physiological data indicates a blood pressure above a predefined blood pressure level.

In some aspects, the techniques described herein relate to a computer-implemented method, further including: providing the analyzed one or more of the audial data, the image data, and the physiological data to an ensemble learner configured to generate a stroke risk for the subject; receiving the generated stroke risk at a mobile device associated with the subject and associated with capture of one or more of the audial data, the image data, and the physiological data; and in response to determining that the generated stroke risk is above a predefined stroke threshold, causing the mobile device to execute a call or generate and send a text to an emergency contact from a contact list configured on the mobile device.

In some aspects, the techniques described herein relate to a computer-implemented method, wherein: the audial data includes one or more utterances captured in near real time by a microphone of a mobile device associated with the subject; the image data includes still images or video data representing at least a portion of a face of the subject captured in near real time by the mobile device; and the physiological data includes blood pressure data or blood oxygen data for the subject that is captured by a wearable device in communication with the mobile device.

In some aspects, the techniques described herein relate to a computer-implemented method, wherein the wearable device is a smart watch having a blood pressure monitoring device configured to monitor blood pressure for the subject.

In some aspects, the techniques described herein relate to a system for predicting stroke symptoms for a subject, the system including: at least one processor; and memory storing instructions that, when executed by the at least one processor, cause the system to execute instructions including: receiving audial data representing one or more utterances of the subject; receiving image data representing one or more images of at least a portion of a face of the subject; receiving physiological data associated with the subject; predicting, based on a plurality of predefined stroke symptoms and at least two of: the audial data, the image data, and the physiological data, a likelihood of the subject is experiencing or will imminently experience one or more of the plurality of predefined stroke symptoms; and in response to determining that the likelihood is above a threshold level associated with one or more of the plurality of predefined stroke symptoms, causing generation of an alert for the subject and an alert for one or more emergency contacts corresponding to the subject.

In some aspects, the techniques described herein relate to a system, wherein the prediction includes accessing an ensemble learner configured to: provide the image data to a first machine learning model to generate analyzed image data for the subject; provide the audial data to a second machine learning model to generate analyzed audial data for the subject; provide the physiological data to a third machine learning model to generate analyzed physiological data for the subject; generate, based on the analyzed image data, the analyzed audial data, and the analyzed physiological data, a classifier configured to generate an indication of the subject experiencing one or more of the plurality of predefined stroke symptoms; and generating, using the classifier, a likelihood of the subject experiencing a stroke event, the likelihood being provided as output to a mobile device associated with the subject or a device associated with the one or more emergency contacts corresponding to the subject.

In some aspects, the techniques described herein relate to a system, wherein the prediction includes accessing an ensemble learner configured to: provide the image data to a machine learning model; receive, from the machine learning model and based on the provided image data, a risk level of the subject experiencing facial asymmetry associated with experiencing a stroke; and generate, based on the risk level, the predicted likelihood as output to a mobile device associated with the subject or a device associated with the one or more emergency contacts corresponding to the subject.

In some aspects, the techniques described herein relate to a system, wherein the image data includes still images or video data representing at least a portion of the face of the subject captured by the mobile device associated with the subject.

In some aspects, the techniques described herein relate to a system, wherein the image data is captured by a front facing camera of the device associated with the subject, the front facing camera capturing the image data during access of a video application on the mobile device associated with the subject.

In some aspects, the techniques described herein relate to a system, wherein the physiological data includes blood pressure data or blood oxygen data for the subject, the physiological data being captured by a wearable device in communication with a mobile device associated with the subject.

In some aspects, the techniques described herein relate to a system, wherein the prediction includes accessing an ensemble learner configured to: provide the audial data, the image data, and the physiological data to a machine learning model; receive, from the machine learning model and based on the provided audial data, the image data, and the physiological data, a risk level of the subject experiencing a stroke or imminently experiencing one or more of the plurality of predefined stroke symptoms.

In some aspects, the techniques described herein relate to a system, wherein the instructions further include analyzing one or more of: the audial data to determine whether the audial data exhibits speech dysarthria; the image data to determine whether the image data exhibits facial asymmetry; and the physiological data to determine whether the physiological data indicates a blood pressure above a predefined blood pressure level.

In some aspects, the techniques described herein relate to a system, wherein the instructions further include: providing the analyzed one or more of the audial data, the image data, and the physiological data to an ensemble learner configured to generate a stroke risk for the subject; receiving the generated stroke risk at a mobile device associated with the subject and associated with capture of one or more of the audial data, the image data, and the physiological data; and in response to determining that the generated stroke risk is above a predefined stroke threshold, causing the mobile device to execute a call or generate and send a text to an emergency contact from a contact list configured on the mobile device.

In some aspects, the techniques described herein relate to a system, wherein: the audial data includes one or more utterances captured in near real time by a microphone of a mobile device associated with the subject; the image data includes still images or video data representing at least a portion of a face of the subject captured in near real time by the mobile device; and the physiological data includes blood pressure data or blood oxygen data for the subject that is captured by a wearable device in communication with the mobile device.

In some aspects, the techniques described herein relate to a system, wherein the wearable device is a smart watch having a blood pressure monitoring device configured to monitor blood pressure for the subject.

In some aspects, the techniques described herein relate to a non-transitory computer-readable storage medium storing instructions that, when executed by at least one processor, cause the at least one processor to predict stroke symptoms for a subject by executing instructions including: receiving audial data representing one or more utterances of the subject; receiving image data representing one or more images of at least a portion of a face of the subject; receiving physiological data associated with the subject; predicting, based on a plurality of predefined stroke symptoms and at least two of: the audial data, the image data, and the physiological data, a likelihood of the subject is experiencing or will imminently experience one or more of the plurality of predefined stroke symptoms; and in response to determining that the likelihood is above a threshold level associated with one or more of the plurality of predefined stroke symptoms, causing generation of an alert for the subject and an alert for one or more emergency contacts corresponding to the subject.

In some aspects, the techniques described herein relate to a non-transitory computer-readable storage medium, wherein the prediction includes accessing an ensemble learner configured to: provide the image data to a first machine learning model to generate analyzed image data for the subject; provide the audial data to a second machine learning model to generate analyzed audial data for the subject; provide the physiological data to a third machine learning model to generate analyzed physiological data for the subject; generate, based on the analyzed image data, the analyzed audial data, and the analyzed physiological data, a classifier configured to generate an indication of the subject experiencing one or more of the plurality of predefined stroke symptoms; and generating, using the classifier, a likelihood of the subject experiencing a stroke event, the likelihood being provided as output to a mobile device associated with the subject or a device associated with the one or more emergency contacts corresponding to the subject.

In some aspects, the techniques described herein relate to a non-transitory computer-readable storage medium, wherein the prediction includes accessing an ensemble learner configured to: provide the image data to a machine learning model; receive, from the machine learning model and based on the provided image data, a risk level of the subject experiencing facial asymmetry associated with experiencing a stroke; and generate, based on the risk level, the predicted likelihood as output to a mobile device associated with the subject or a device associated with the one or more emergency contacts corresponding to the subject.

In some aspects, the techniques described herein relate to a non-transitory computer-readable storage medium, wherein the image data includes still images or video data representing at least a portion of the face of the subject captured by the mobile device associated with the subject.

In some aspects, the techniques described herein relate to a non-transitory computer-readable storage medium, wherein the image data is captured by a front facing camera of the device associated with the subject, the front facing camera capturing the image data during access of a video application on the mobile device associated with the subject.

In some aspects, the techniques described herein relate to a non-transitory computer-readable storage medium, wherein the physiological data includes blood pressure data or blood oxygen data for the subject, the physiological data being captured by a wearable device in communication with a mobile device associated with the subject.

In some aspects, the techniques described herein relate to a non-transitory computer-readable storage medium, wherein the prediction includes accessing an ensemble learner configured to: provide the audial data, the image data, and the physiological data to a machine learning model; receive, from the machine learning model and based on the provided audial data, the image data, and the physiological data, a risk level of the subject experiencing a stroke or imminently experiencing one or more of the plurality of predefined stroke symptoms.

In some aspects, the techniques described herein relate to a non-transitory computer-readable storage medium, wherein the instructions further include analyzing one or more of: the audial data to determine whether the audial data exhibits speech dysarthria; the image data to determine whether the image data exhibits facial asymmetry; and the physiological data to determine whether the physiological data indicates a blood pressure above a predefined blood pressure level.

In some aspects, the techniques described herein relate to a non-transitory computer-readable storage medium, wherein the instructions further include: providing the analyzed one or more of the audial data, the image data, and the physiological data to an ensemble learner configured to generate a stroke risk for the subject; receiving the generated stroke risk at a mobile device associated with the subject and associated with capture of one or more of the audial data, the image data, and the physiological data; and in response to determining that the generated stroke risk is above a predefined stroke threshold, causing the mobile device to execute a call or generate and send a text to an emergency contact from a contact list configured on the mobile device.

In some aspects, the techniques described herein relate to a non-transitory computer-readable storage medium, wherein: the audial data includes one or more utterances captured in near real time by a microphone of a mobile device associated with the subject; the image data includes still images or video data representing at least a portion of a face of the subject captured in near real time by the mobile device; and the physiological data includes blood pressure data or blood oxygen data for the subject that is captured by a wearable device in communication with the mobile device.

In some aspects, the techniques described herein relate to a non-transitory computer-readable storage medium, wherein the wearable device is a smart watch having a blood pressure monitoring device configured to monitor blood pressure for the subject.

BRIEF DESCRIPTION OF THE DRAWINGS

The foregoing is a summary, and thus, necessarily limited in detail. The above-mentioned aspects, as well as other aspects, features, and advantages of the present technology are described below in connection with various implementations, with reference made to the accompanying drawings.

FIG. 5 illustrates a flow diagram of an example process for predicting stroke symptoms for a subject.

Figure 1:
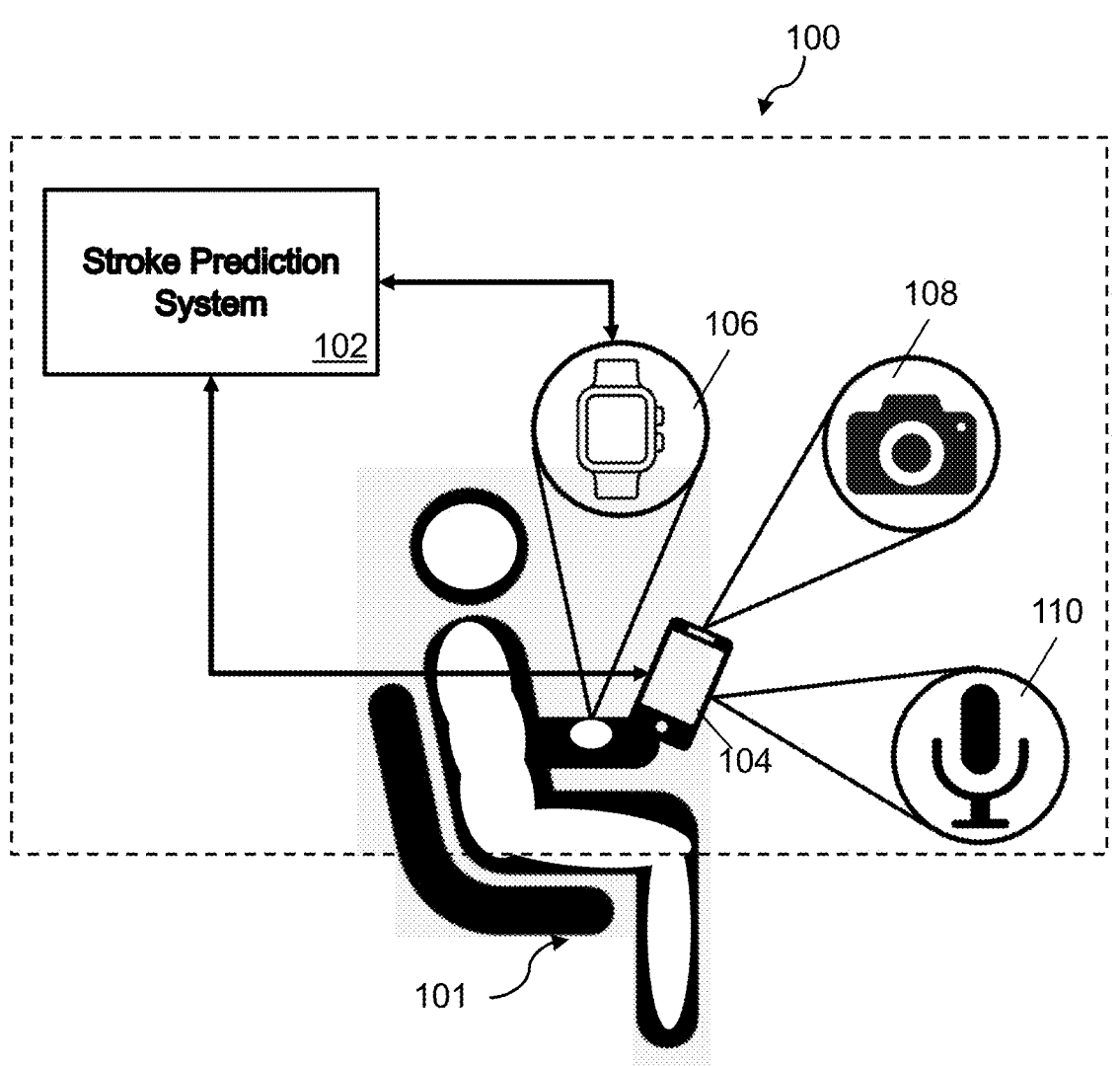
FIG. 1 illustrates a schematic diagram of an example stroke monitoring system for detecting stroke events and/or stroke symptoms for a subject.

The illustrated implementations are merely examples and are not intended to limit the disclosure. The schematics are drawn to illustrate features and concepts and are not necessarily drawn to scale.

DETAILED DESCRIPTION

The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Disclosed herein are systems and methods for detecting one or more stroke symptoms in a subject at or substantially near onset of such symptoms. For example, the systems and methods described herein may use audial data, image data, and/or physiological data to determine whether a subject (e.g., patient, user, etc.) is experiencing or will imminently experience one or more stroke symptoms and/or an actual stroke event. Upon detecting the one or more stroke symptoms (or stroke event), the systems and methods described herein may generate and send one or more communications to emergency services and/or emergency contacts associated with the subject. For example, if one or more stroke symptoms of a user are detected by the systems described herein, one or more messages may be generated and sent to one or more emergency contacts in which the user has previously configured with respect to a mobile phone, or other computing device. In some embodiments, the system may instead, or additionally, generate and send one or more messages to an emergency services provider, a physician, or the like. In some embodiments, the systems and methods described herein can monitor a subject over time using one or more sensors, cameras, or microphones to determine stroke event occurrences or stroke onset to facilitate early intervention and/or treatment of stroke events and/or related stroke symptoms.

Prominent indicators of stroke encompass facial paralysis, manifested as facial asymmetry (e.g., facial asymmetrical drooping), impaired speech (e.g., dysarthria), elevated blood pressure (e.g., above about 135/90 mmHg to about 140/90 mmHg), vision disturbances, seizures, walking or balance disturbances, and/or weakened arm muscles. Although the actual blood clot causing the stroke is not visible, the symptoms enumerated previously can be identified by the subject or bystanders. However, even if the subject is exhibiting symptoms, the subject may not recognize the cause or the potential for long-term damage. Stroke symptoms can unfold quickly, within minutes, or more gradually, within hours. Depending on the severity of the symptoms, the subject may not opt to go to the emergency room once stroke symptoms present, wasting valuable time that could be used for treatment. For this reason, it is of interest for the health of the subject to detect symptoms and react as quickly as possible. If the time between a subject detecting symptoms and arriving at a hospital can be reduced, the chance of survival of the subject increases and the likelihood of irreversible brain damage is reduced.

The systems and methods described herein solve a technical problem of early stroke detection by proactively monitoring a user for symptoms of stroke and triggering contact of one or more emergency contacts immediately upon discovery of such symptoms. In particular, the technical problem sought to be solved by the present disclosure is to provide non-invasive, near real time, and/or continuous stroke monitoring for a user utilizing devices that a user may regularly use and/or wear. Such devices may include, but are not limited to, a mobile phone (e.g., a smart phone), a tablet, a laptop, a desktop, a smart watch, and/or a health or fitness tracker. An example technical solution provided by the embodiments described herein includes employing at least one sensor, at least one image, and/or one or more audible utterances as a basis in which to generate a likelihood of a stroke event, an onset of a stroke event (e.g., symptoms of stroke), and/or an overall predicted stroke risk for the subject.

Stroke Monitoring and Prediction System

FIG. 1 illustrates a schematic diagram of an example stroke monitoring system 100 for detecting stroke events and/or stroke symptoms for a subject 101. The stroke monitoring system 100 may detect, receive, or otherwise obtain input associated with a subject. The input may be used to determine whether the subject is experiencing a stroke event or one or more stroke symptoms, or imminently experiencing a stroke event or one or more stroke symptoms. The input may include any one or more of: physiological data (e.g., heart rate, blood pressure, blood oxygen data, body temperature, blood glucose, and/or patterns thereof, etc.), image data, audial data, medical data (e.g., emergency medical records, test results, clinician entered data, etc.), and/or contacts data (e.g., emergency contacts, user contacts, telephone numbers, emails, addresses, etc.). The stroke monitoring system 100 can include a stroke prediction system 102, a mobile device 104, and a wearable device 106. In some embodiments, the stroke monitoring system 100 may execute as software and/or hardware onboard stroke prediction system 102. In some embodiments, the stroke monitoring system 100 may execute as software and/or hardware onboard mobile device 104. In some embodiments, the stroke monitoring system 100 may execute as software and/or hardware onboard wearable device 106. In some embodiments, the stroke monitoring system 100 may execute as software and/or hardware separate from both devices 104, 106, and/or stroke prediction system 102, but may receive data from one or both devices 104, 106 and/or stroke prediction system 102 to detect and/or determine stroke risks, stroke symptoms, or stroke events for a subject in substantially real time.

The mobile device 104 and/or the wearable device 106 may include (or be communicatively coupled to) one or more sensors (e.g., sensors 162 and/or sensors 172). The sensors (e.g., sensors 162 and/or sensors 172) may function to capture or sense image data, audial data, and/or physiological data that may be used by system 100 to detect and/or determine stroke risks, stroke symptoms, or stroke events for the subject in substantially real time. For example, one or more sensors (e.g., sensors 172) or devices coupled to mobile device 104 and/or wearable device 106 may measure, characterize, or detect physical responses (e.g., stroke events, face or body movements (or lack thereof), facial expressions, heart rate, blood pressure, blood oxygen levels, stress response, heat stroke, seizure, menopause, diabetes, etc.) for a subject. The subject may be wearing the wearable device 106 and/or utilizing or be within range of sensors or devices onboard mobile device 104, each or both of which may be: part of stroke monitoring system 100, separate from stroke monitoring system 100, or in communication with stroke monitoring system 100. In some embodiments, the sensors (e.g., sensors 162 and/or sensors 172) can be integrated with (or communicatively coupled to) the wearable device 106. In some embodiments, the sensors (e.g., sensors 162 and/or sensors 172) can be integrated with (or communicatively coupled to) the mobile device 104.

In some embodiments, some or all of the sensors (e.g., sensors 162 and/or sensors 172) may be physically separate from the wearable device 106, for example, as part of mobile device 104 or another device in communication with stroke monitoring system 100. The sensors described herein can be communicatively coupled to the mobile device 104 including wired and/or wireless connections. The stroke monitoring system 100 may also connect with other external computing devices, cloud platforms, clients, servers, or the like. Alternatively, or additionally, the stroke monitoring system 100 may integrate with third-party devices and/or services. The sensors (e.g., sensors 162 and/or sensors 172) may include any one or more of temperature sensors, strain gauge sensors, image sensors (e.g., camera 108), infrared sensors, inertial measurement unit sensors (or other movement detecting sensor), heart rate sensors, microphones (e.g., microphone 110), or any combination thereof.

The stroke prediction system 102 may generate a likelihood of experiencing a stroke event or a likelihood of imminently experiencing a stroke event. In one non-limiting example of using stroke monitoring system 100 to identify a stroke event, input may be received by the stroke prediction system 102. For example, one or more images of a portion of the subject 101 may be received from camera 108 of mobile device 104. The camera 108 may be a front-facing camera, for example to capture all or a portion of a face of the subject 101 while a user accesses mobile device 104. In particular, the camera 108 may, with user permission, capture image data including any number of images, video, or the like of the subject 101. In some embodiments, the camera 108 may capture such image data while the subject 101 accesses one or more other applications or content on the device 104. At substantially the same time, one or more utterances that a user is performing may be captured by the microphone 110 of device 104. In addition, physiological data for the subject 101 (such as blood pressure data) may be captured by wearable device 106. Such physiological data may also be captured at substantially the same time as other sensor input. In some embodiments, data from the camera 108, microphone 110, and/or wearable device 106 may be substantially, simultaneously captured at intervals of a few milliseconds (e.g., about 3 milliseconds to about 20 milliseconds).

In some embodiments, the image data described herein may be captured from any number or type of camera. For example, the one or more cameras 108 may include any or all cameras surrounding a subject. For example, the one or more cameras 108 may include one or more phone cameras, tablet cameras, laptop cameras, television cameras, assistant device cameras, Internet of Things (IoT) device cameras, in-home cameras, security cameras, or the like. Similarly, the audial data described herein may be captured from any number or type of microphone. For example, the audial data may be captured by any one or more microphones surrounding a subject. For example, the audial data may be captured from one or more smart phones, tablets, laptops, televisions, assistant devices, Internet of Things (IoT) devices, in-home camera devices, security camera devices, or the like. When capturing such image or audial data, user permissions are preconfigured to ensure user/subject privacy and knowledge of such data capture.

The stroke prediction system 102 may assess one or more individual image frames captured by the camera 108 and may use one or more neural networks (NNs 139) to process the image data. For example, a first NN may represent a visual machine learning (ML) model trained on a dataset of face images (e.g., assigned to stroke symptoms or assigned to no stroke symptoms). The dataset and training may be used to distinguish between symmetrical and asymmetrical faces, where asymmetry indicates facial drooping and paralysis (e.g., possible stroke symptoms) and symmetrical indicates no stroke symptoms. The first NN may use the captured image data to generate a first prediction (e.g., representing analyzed image data) of whether or not the subject is experiencing (or may imminently experience) a stroke event.

Additionally, one or more speech samples from the microphone on device 104 may be processed in a second NN. The second NN may represent an audial ML model trained on a dataset to distinguish between typical and dysarthric (i.e., slurred) speech (e.g., an audial stroke symptom). The second NN may use the captured audial data (e.g., speech samples) to generate a second prediction (e.g., representing analyzed audial data) of whether or not the subject is experiencing (or may imminently experience) a stroke event.

Furthermore, the physiological data (e.g., blood pressure data) of the subject 101 may be captured by the wearable device 106 and may be analyzed by a third NN that may represent a physiological data ML model capable of determining whether physiological symptoms over time exceed particular predefined limits. Such limits may be indicated in predetermined thresholds entered by clinicians and/or provided in training data that may be generated based at least in part on medical thresholds set by medical standards, historical medical data, or the like. Example thresholds may include an elevated blood pressure between or above about 135/90 mmHg to about 136/90 mmHg; about 136/90 mmHg to about 137/90 mmHg; about 137/90 mmHg to about 138/90 mmHg; about 138/90 mmHg to about 139/90 mmHg; about 139/90 mmHg to about 140/90 mmHg or higher. Example blood oxygen level thresholds may include a blood oxygen saturation below about 95 percent. In some embodiments, the image data from camera 108 of mobile device 104 may also be provided to the third NN to supplement the physiological data from the wearable device 106. The third NN may use the captured physiological data (e.g., blood pressure data) and/or the image data to generate a third prediction (e.g., representing analyzed physiological data) of whether or not the subject is experiencing a stroke event.

The stroke prediction system 102 may compile the first prediction, the second prediction, and the third prediction into a classifier that may generate an indication of whether or not the subject is experiencing (or may imminently experience) a stroke event. In some embodiments, the stroke prediction system 102 may use the generated classifier to generate an indication of a presence or absence of stroke symptoms. In some embodiments, the stroke prediction system 102 compiles each of the first, second, and third predictions into separate classifiers to be used to generate an indication of a presence or absence of stroke symptoms.

In some embodiments, the stroke prediction system 102 may use the generated classifier to generate a likelihood of experiencing a stroke event or a likelihood of imminently experiencing one or more stroke symptoms. In some embodiments, the stroke prediction system 102 compiles each of the first, second, and third predictions into separate classifiers to be used to generate a likelihood of experiencing a stroke event or a likelihood of imminently experiencing one or more stroke symptoms.

In some embodiments, the stroke prediction system 102 may use the generated classifier to generate a stroke risk score for a subject indicating a level of risk of experiencing a stroke event. In some embodiments, the stroke prediction system 102 compiles each of the first, second, and third predictions into separate classifiers to be used to generate a stroke risk score for a subject indicating a level of risk of experiencing a stroke event.

In operation, the stroke prediction system 102 may generate, based on the analyzed image data, the analyzed audial data, and the analyzed physiological data, one or more classifiers that may be used to generate an indication that the subject 101 is currently experiencing one or more of the plurality of predefined stroke symptoms. The stroke prediction system 102 may use the classifier(s) to generate a likelihood of the subject experiencing a stroke event and/or to generate a stroke risk for the subject. The likelihood may be provided as output to the mobile device 104 and/or wearable device 106 that is associated with the subject 101, or another device associated with the one or more contacts corresponding to the subject.

Figure 2:
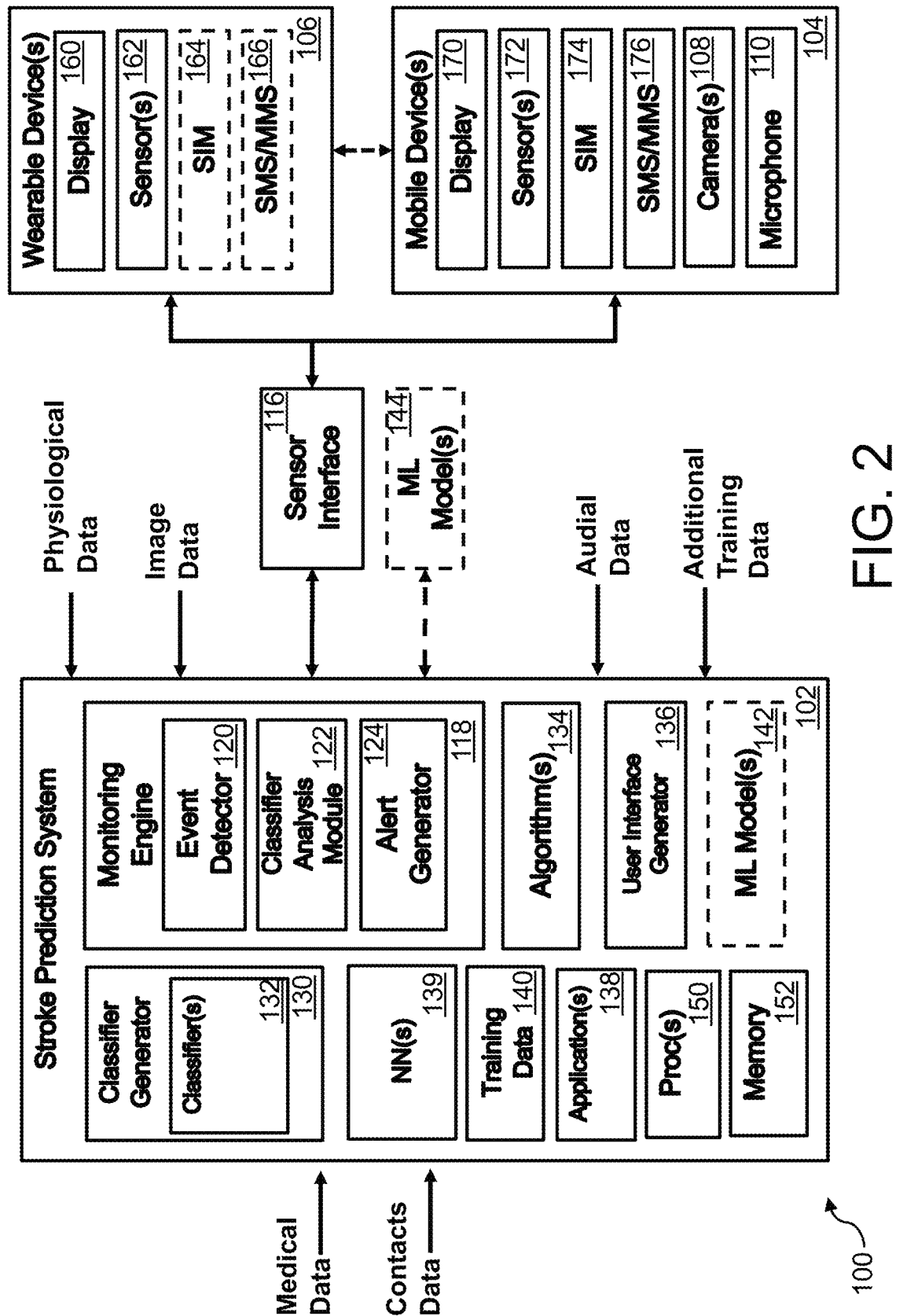
FIG. 2 illustrates a block diagram of a computing environment for the example stroke monitoring system of FIG. 1.

FIG. 2 illustrates a block diagram of a computing environment for the example stroke monitoring system 100 of FIG. 1. The stroke monitoring system 100 includes the stroke prediction system 102 communicatively coupled to the wearable device 106 and the mobile device 104. In some embodiments, a sensor interface 116 may enable sensor data to be communicated between the stroke prediction system 102 and the mobile device and/or the wearable device 106. In some embodiments, the mobile device 104 may be communicatively coupled to the wearable device 106 to share data.

The stroke prediction system 102 may include a monitoring engine 118 for monitoring stroke risk and/or stroke symptoms exhibited by the subject 101. In some embodiments, the monitoring may include receiving monitored data from one or more sensors or devices associated with the subject 101. The received data can be monitored over time to determine stroke risk and/or the exhibition of stroke symptoms by the subject 101. Although the monitoring engine 118 is depicted as part of the stroke prediction system 102, in some embodiments, the monitoring engine 118 may instead be part of the wearable device 106, part of the mobile device 104, or may be a standalone device.

The monitoring engine 118 may determine when events or data changes occur at one or more of the sensors (e.g., sensors 162) on wearable device 106 and/or sensors (e.g., sensors 172) on mobile device 104 through a sensor interface 116, for example. The sensor interface 116 may store instructions to carry out operations pertaining to received sensor signals from one or more of the sensors 162 and/or sensors 172 and/or other sensors in communication with system 102, mobile device 104, and/or wearable device 106. For example, the instructions may enable interaction with one or more processors 150 (or processors onboard mobile device 104 and/or wearable device 106), memory 152 (or memory onboard mobile device 104 and/or wearable device 106), and/or sensors 162 and/or sensors 172 to communicate sensor data amongst system 102 and devices 104, 106. The sensor data may be obtained from the sensors 162 and/or sensors 172 sensing/capturing recordings and measurements.

The monitoring engine 118 may include an event detector 120, a classifier analysis module 122, and an alert generator 124. The event detector 120 may monitor and detect biological signals and/or stroke events. The signals and/or stroke events may pertain to data captured by sensors 162 onboard device 106 and/or sensors 172 onboard device 104, or another external sensor in communication with system 102, device 106, or device 104 to monitor or characterize the signals or determine whether a signal has changed or a stroke event is impending or has occurred.

The classifier analysis module 122 may function in combination with the event detector 120 and the classifier generator 130 to determine whether an event (or change in biological data) is to trigger an alert, a message, or other communication to warn a subject or those associated with a subject about an impending event, a stroke event, or a change in a signal pertaining to one or more stroke symptoms, for example. The trigger may be determined based at least in part on one or more separate or combined classifiers 132.

The alert generator 124 may receive an indication of whether to trigger an alert and in response, may trigger the alert for the subject on device 104 or for emergency contacts set up by the subject. For example, a blood pressure sensor (e.g., sensor 162) may function with the monitoring engine 118 to monitor and obtain blood pressure and/or blood oxygen data at a particular skin surface site associated with the wearable device 106. The monitoring engine 118 may trigger the alert generator 124 to generate an alert in response to determining that a monitored blood pressure has reached or exceeded a predefined threshold, as described elsewhere herein.

The alert generator 124 may alert the subject wearing the wearable device 106 (e.g., which may also be the user of device 104) and/or alert a third party of an event, available physiological data, and/or a change in data. The third party may include one or more emergency contacts that the subject configured in devices 104 and/or 106, other users associated with the subject wearing device 106 and/or using device 104, and/or a service or clinician in communication with device 104, device 106, and/or system 102.

The alerts, messages, texts, and/or phone calls triggered by the monitoring system 100 and/or the stroke detection system 102 are generated and sent with prior permissions from the subject 101. For example, the triggering of sharing of patient medical data, personal information, and events or symptom occurrences is based on the subject configuring a prior permission to allow systems 100, 102 to comply with Health Insurance Portability and Accountability Act (HIPPA) or other healthcare privacy system. Accordingly, the systems and methods described herein provide compliance with HIPPA, and other privacy requirements regarding patient medical data, or other personal information. For example, the processes 300, 400, and 500 are executed in such a fashion to be HIPPA compliant and requisite warnings are provided to protect the information contained in system 100 and system 102 in compliance with HIPPA or other healthcare privacy system.

In some embodiments, the alert may be an audible sound, a visual indicator, and/or a message (e.g., email, SMS/MMS text message using SIM 174 and/or an SMS/MMS module 176 on mobile device 104 and/or optional SIM 164 and/or an optional SMS/MMS module 166 on wearable device 106, etc.) to the subject or third party. In some embodiments, the alert may be a notification sent to emergency services or clinicians. For example, such notifications may alert emergency services or clinicians and may include data with medical history, monitoring history, and event history. The notifications may be transmitted directly to emergency services or clinician computing systems, either directly from the wearable device 106 or from mobile device 104, initiated by a signal from the wearable device 106 and/or a signal from the mobile device 104. In addition to alerts, the wearable device 106 and/or mobile device 104 may additionally instruct a user to undertake or automatically activate certain treatments or steps based detected output from sensors 162 and/or sensors 172.

The stroke prediction system 102 may further include a classifier generator 130 that may generate one or more classifiers 132 for use in determining whether a subject exhibits stroke symptoms and/or stroke risks. Example classifiers 132 may include any number of neural network outputs combined with logic to generate a prediction or likelihood of the subject 101 experiencing a stroke event and/or one or more stroke symptoms. In some embodiments, the one or more classifiers may be used in combination to determine a stroke risk or event likelihood. For example, the classifiers 132 be used to employ a combination of: data augmentation (e.g., using an adversarial model), facial key point detection, and/or speech parsing. For example, one or more classifiers 132 may be generated to analyze input about the subject 101 including, but not limited to image data from device 104, audial data from device 104, and/or physiological data from device 106. In some embodiments, the system 100 may use a generative adversarial model to augment any or all of the received input data. For example, the system 100 may augment image data to depict facial arrangement (e.g., symptoms, drooping, etc.) associated with stroke. Augmented image data may include analyzing particular facial features to determine locations of such features and then applying a change to such a feature to approximate an image of a change in one or more facial features (or other body part) to emulate one or more stroke symptoms. In some embodiments, such augmentation may be performed to generate examples of adversarial instances indicating stroke (e.g., erroneous image-based stroke features) and provide those examples to the NNs 139, ML models 142 and/or ML models 144 with labels indicating stroke symptoms, not stroke symptoms, or the like. This process may facilitate stroke symptom recognition while preventing inaccurate facial feature (or other body part) classification.

The system 100 may additionally use a generative adversarial model to augment audial data. For example, the system 100 may augment received/detected audial data of the subject 101 to mimic audial sounds that may be typical of experiencing a stroke, including, but not limited to, slurring of words, partial use of one side of the mouth resulting in modified enunciation and/or pronunciations, etc. Augmented audial data may include analyzing particular audial utterances from the subject to determine typical speech patterns, enunciation patterns, pronunciation patterns, voice, etc., and then applying a change to such utterances to approximate utterances that may emulate one or more audial stroke symptoms. In some embodiments, such augmentation may be performed to generate examples of adversarial instances indicating stroke (e.g., erroneous audial-based stroke utterances) and provide those examples to the NNs 139, ML models 142 and/or ML models 144 with labels indicating stroke symptoms, not stroke symptoms, or the like. This process may facilitate stroke symptom recognition while preventing inaccurate audial utterance classification.

The system 100 may additionally use a generative adversarial model to augment physiological data (e.g., heart rate, blood pressure, blood oxygen data, body temperature, blood glucose, gait, arm movement, leg movement, body portion movement, and/or patterns thereof, etc.).

For example, the system 100 may augment received/detected physiological data of the subject 101 to mimic physiological symptoms that may be typical of experiencing a stroke. Augmented physiological data may include analyzing particular physiological data from the subject to determine typical physiological measurements or patterns and then applying a change to such measurements or patterns to approximate physiological changes that may emulate one or more physiologically detectable stroke symptoms. In some embodiments, such augmentation may be performed to generate examples of adversarial instances indicating stroke (e.g., erroneous physiological-based stroke symptom) and provide those examples to the NNs 139, ML models 142 and/or ML models 144 with one or more class labels indicating stroke symptoms, not stroke symptoms, or the like. This process may facilitate stroke symptom recognition while preventing inaccurate physiological symptom classification. In such examples, image data may also be used in combination with the physiological data as a basis in which to augment symptoms and train the models described herein.

In general, the modified image data, audial data, and/or physiological data generated by the adversarial model may be used as training data 140 generated by system 102 and/or used or provided as additional training data from an external source. For example, output from any of the adversarial models described herein may be used to train a stroke detection model for use with the stroke prediction system 102.

In some embodiments, the neural networks described herein are used without a classifier and instead the classifier analysis module 122 may be used to generate a stroke risk or event likelihood. Conventional classifiers typically utilize convolution networks and/or a singular neural network for analyzing fewer variables associated with the health of the subject than those described herein.

The stroke prediction system 102 may further include one or more algorithms 134. The algorithms 134 may include computer executable code adapted to carry out any of the methods described herein on any of the processors described herein. In some embodiments, the algorithms 134 utilize monitoring engine 118, classifier generator 130 and/or classifiers 132, NNs 139, ML models 142, and/or optional ML models 144 to generate output. In operation, the algorithms 134 may operate on particular sensor data (e.g., obtained from sensors 162, sensors 172, or another sensor in communication with system 102). The operations may prepare the data (e.g., preprocess) and/or otherwise analyze the data to generate predictions (e.g., stroke symptoms, stroke risks, event occurrence, etc.). The algorithms 134 may control operations on mobile device 104 and/or wearable device 106. Such examples may include outputting one or more signals to trigger indications, alerts, and/or messages associated with detected sensor data or changes in sensor data. In some embodiments, the algorithms 134 may include or control one or more ensemble learners The stroke prediction system 102 may further include a user interface generator 136. The user interface generator 136 may interact with one or more processors 150 (or processors onboard mobile device 104 and/or wearable device 106), memory 152 (or memory onboard mobile device 104 and/or wearable device 106), and/or sensors 162 and/or sensors 172. The user interface generator 136 may generate user interfaces for display to a user of the mobile device 104 and/or the wearable device 106 or other user associated with the mobile device 104 and/or the wearable device 106. The user interfaces generated by the user interface generator 136 may include patient data and medical records, sensor measurements and data, instructions, diagnosis data, or the like. The user interfaces generated by generator 136 may be presented on a display 170 of mobile device 104, and/or on a display 160 of the wearable device 106 and/or on a display of a companion device such as a laptop, tablet, or computer when arranged and permitted by the subject 101, for example, to receive information and user interfaces pertaining to a condition and/or symptoms being experienced by the subject 101.

In some embodiments, the user interfaces generated by generator 136 may additionally be displayed on a device associated with a contact indicated by the user to receive the user interface content responsive to a detected event or symptom. For example, the system 100 may generate and send a text message or a voice message for provision to a device of an indicated contact. The content of the message may provide an indication that the subject 101 is currently experiencing or imminently experiencing a stroke event and/or one or more stroke symptoms. Further, the message may indicate that the subject 101 may need to seek treatment immediately. Such messages may follow security guidelines to protect medical data or other subject data, as described elsewhere herein.

The stroke prediction system 102 may further include applications 138. The applications 138 may represent one or more software applications that may be installed on (or accessed from) the mobile device 104 and/or the wearable device 106. The applications 138 may be used to present user interfaces generated by user interface generator 136.

The stroke prediction system 102 may further include training data 140. In some embodiments, the training data 140 may instead, or additionally, be accessed external to the stroke prediction system 102. The training data 140 may include one or more datasets of face images to distinguish between symmetrical and asymmetrical faces. The training data 140 may include one or more speech sample datasets to distinguish between slurred speech and non-slurred speech. The training data 140 may further include physiological value datasets (e.g., blood pressure, blood oxygen, temperature, gait data, balance data, or the like) to distinguish between healthy non-stroke subjects and a subject experiencing or imminently experiencing a stroke. The training data 140 may further include medical record data, aggregated medical record data, clinician input, medication protocols, or the like.

The stroke prediction system 102 may further include optional ML models 142 (e.g., for using or accessing NNs 139, artificial intelligence, etc.). In some embodiments, the optional ML models 142 are instead, or additionally, accessed external to stroke prediction system 102, as shown by ML models 144, and may access or utilize neural NNs 139 or another architecture of neural networks.

The optional ML models 142 and/or optional ML models 144 may use machine learning techniques to estimate stroke symptom activity and/or stroke event occurrences in a subject wearing the wearable device 106 and/or associated with mobile device 104. For example, the ML models 142 may perform analysis, pattern classification, and/or recognition algorithms on sensor signals received from sensors 162 and/or sensors 172 to assess changing properties of physiological changes occurring within the subject 101. Portions of the analyzed signals may be used to generate likelihoods, predictions, risks, or events pertaining to stroke symptoms and/or stroke occurrence. The optional ML models 142 and/or optional ML models 144 may perform one or more operations on sensor data received from sensors 162 and/or sensors 172 including, but not limited to, signal processing and analysis that may employ NNs 139, and algorithms 134.

The stroke prediction system 102 may further include one or more processors 150 and memory 152. The one or more processors 150 may include one or more hardware processors, including microcontrollers, digital signal processors, application specific integrated circuit (ASIC), a field programmable gate array (FPGA) or other programmable logic device, discrete gate or transistor logic, discrete hardware components, or any combination thereof designed to perform the functions described herein and/or capable of executing instructions, such as instructions stored by the memory 152. The processors 150 may also be able to execute instructions for performing communications amongst system 102 and mobile device 104 and/or wearable device 106.

The memory 152 can include one or more non-transitory computer-readable storage media. The memory 152 may store instructions and data that are usable in combination with processors 150 to execute algorithms 134, optional ML models 142, optional ML models 144, and applications 138. The memory 152 may also function to store or have access to the monitoring engine 118, sensor interface 116, and patient/subject data including, but not limited to, physiological signals, image data, audial data, medical data, contacts data, etc., as shown in FIG. 2. Such data may be provided by the subject 101 and/or obtained from device 106, and/or device 104.

The mobile device 104 may be a smart phone, a smart watch, a laptop device, a tablet device, a health or fitness tracker, or other computing device. The wearable device 106 may include a display 160, one or more sensors 162, an optional SIM 164, and an optional SMS/MMS module 166.

The wearable device 106 may be a smart watch, a health or fitness tracker, a wearable band or sensor, or other sensor or computer-based monitoring device. The mobile device 106 may include a display 170, one or more sensors 172, a SIM 174, an SMS/MMS module 176, at least one camera 108, and at least one microphone 110.

Figure 3:
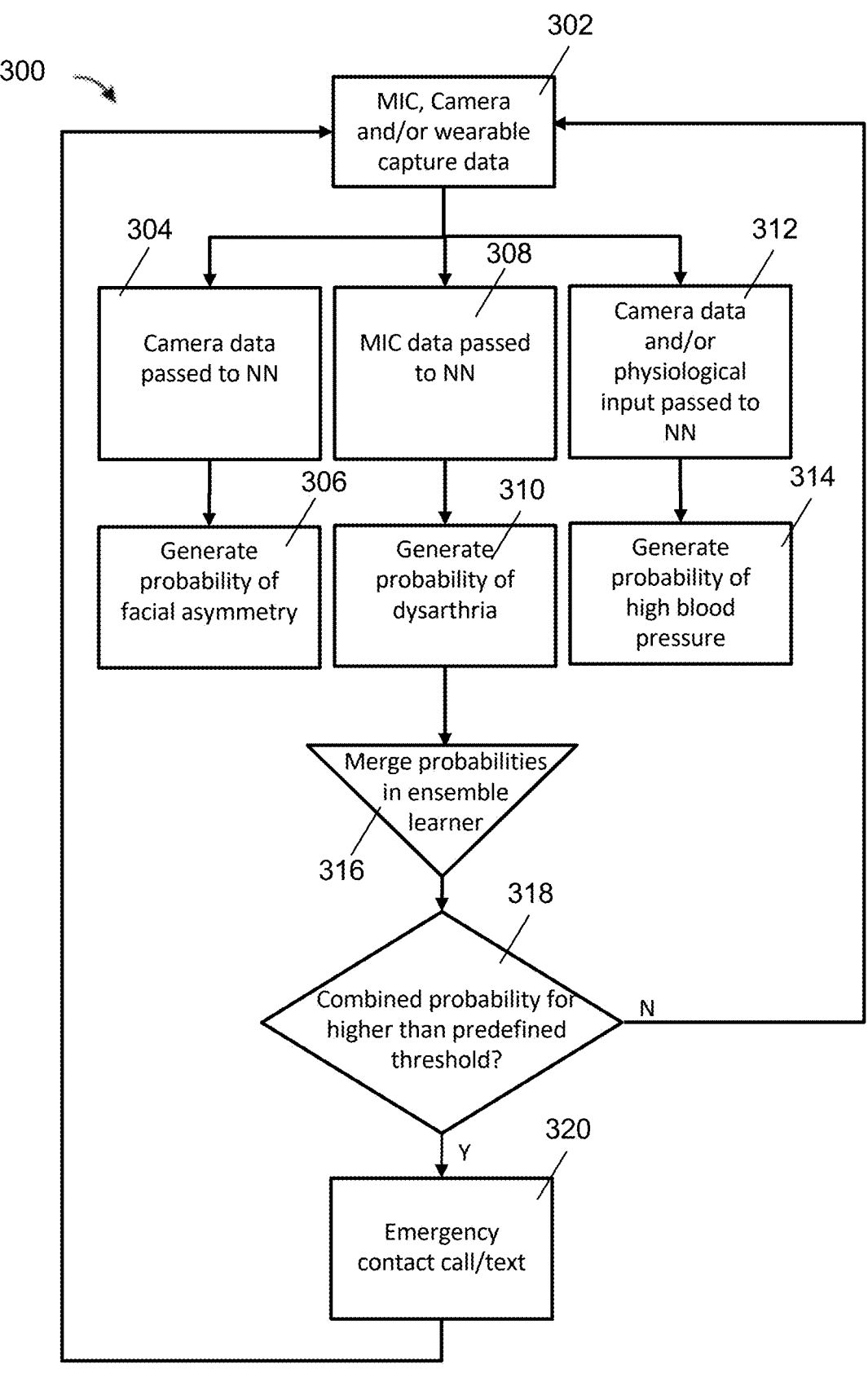
FIG. 3 illustrates an example flow diagram of an example process for monitoring signs of a stroke in a subject.

FIG. 3 illustrates an example flow diagram of an example process 300 for monitoring signs of a stroke in a subject. The process 300 may generally include assessing input regarding a subject, generating probabilities of stroke events and/or stroke symptoms, and triggering messages, indications, phone calls, text messages, or the like in response to determining that the subject is at an elevated risk of a stroke.

In operation, the subject 101, for example, may be holding a personal computing device, such as a mobile device 104. The subject 101 may be substantially facing a screen and/or the front-facing camera (e.g., one or more cameras 108) and may have access to a microphone (e.g., microphone 110). The subject 101 may also be wearing or may be in proximity to a wearable device (e.g., such as a fitness or health tracker/smart watch shown here as wearable device 106).

At block 302, the process 300 causes the microphone 110, the one or more cameras 108, and the wearable device 106 to capture input data. For example, the input may include audial data captured by the microphone 110, image data captured by the cameras 108, and/or physiological data captured by the wearable device 106. In some embodiments, the input data may be captured at a sample rate of about 3 milliseconds to about 20 milliseconds.

At block 304, the image data may be provided to a first NN (e.g., image data NN 139a). At block 306, the output from the first NN may be used to generate a first probability that the subject 101 is experiencing facial asymmetry.

At block 308, the audial data may be provided to a second NN (e.g., audial data NN 139b). At block 310, the output from the second NN may be used to generate a second probability that the subject 101 is experiencing dysarthria.

At block 312, the image data and/or the physiological data may be provided to a third NN (e.g., physiological data NN). At block 314, the output from the third NN may be used to generate a third probability that the subject 101 is experiencing high blood pressure or other symptom assessed using physiological data and/or image data.

Figure 4:
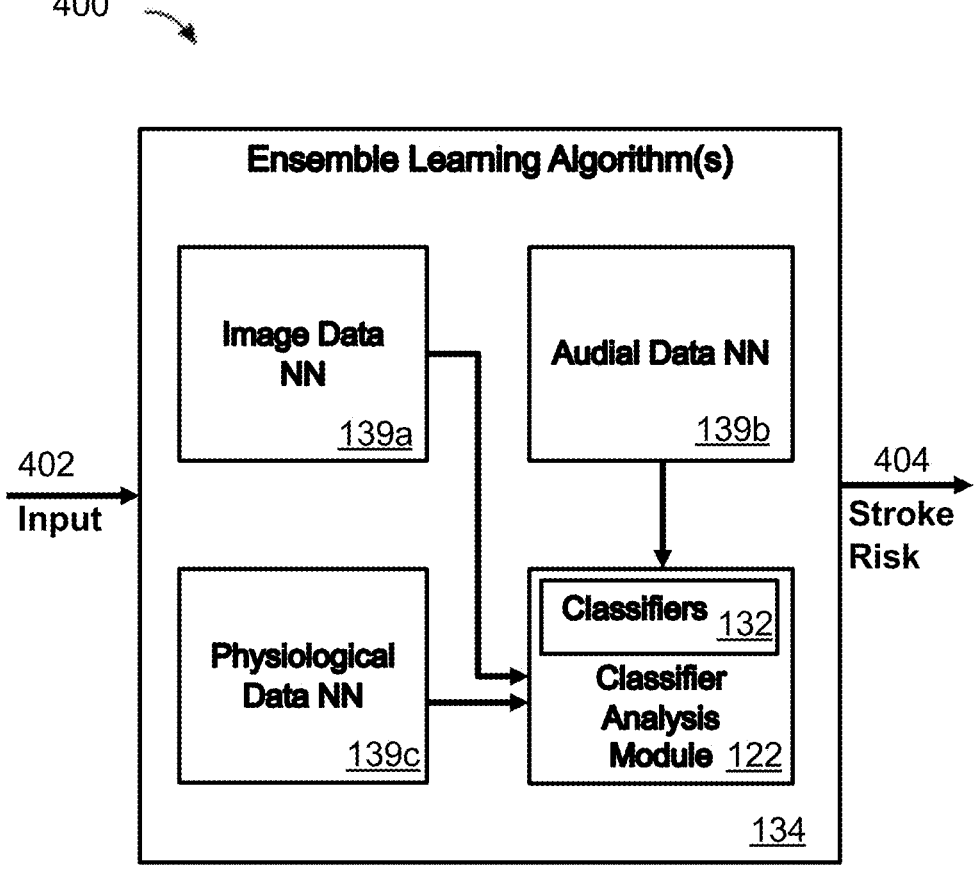
FIG. 4 illustrates a block diagram of example ensemble learning algorithms used by the systems described herein.

At block 316, the process 300 includes combining (e.g., providing) the first probability, the second probability, and the third probability using an ensemble learner (e.g., ensemble learning algorithm 134 of FIG. 4). For example, the ensemble learning algorithms may combine and analyze the first probability, the second probability, and the third probability. At block 318, the process 300 may determine whether the combined/provided probabilities result in an output that is above a predefined symptom threshold. The predefined symptom threshold for image data may include a margin of error for movement of one or more facial features or a margin of error for one or more patterns of movement of one or more facial features. Such margins of error may include about 5 percent to about 10 percent difference in movement of a first eye as compared to a second eye to indicate facial sagging, for example. Other margins of error are of course possible. In some embodiments, a predefined symptom threshold for audial data may include more than 5 percent to about 10 percent of words or utterances are detected to be slurred and as such, the threshold may be triggered if the utterances of the subject increase beyond such threshold levels. In some embodiments, probabilistic thresholds may be utilized with process 300 and system 100, in general. For example, if a likelihood of stroke symptoms being displayed is determined to be above about 70 percent, the system 100 may trigger an alert or message regarding such symptoms and the determined likelihood.

At block 320, if the process 300 determines that the combined probability is above the predefined symptom threshold, then the process 300 causes an emergency contact call, text, indicator, or message to be performed. Instead, if the process 300 determines that the combined probability is at or below the predefined symptom threshold, then the process 300 may return to block 302 to continue capturing data and monitoring for signs of a stroke for the subject 101.

FIG. 4 illustrates a block diagram of example ensemble learning algorithms 134 used by the systems described herein to generate a stroke risk for a subject. The ensemble learning algorithms 134 may include computer executable code adapted to carry out logic for analyzing image data, audial data, physiological data, and classifiers generated based on such data.

In this example, input 402 may be provided to the algorithms 134. The input 402 may include, but is not limited to, image data representing one or more images of at least a portion of a face of the subject, audial data representing one or more utterances of the subject, physiological data (e.g., biometric data including one or more of heart rate, blood pressure, or blood oxygen levels) associated with the subject, medical data associated with the subject, and contacts (e.g., mobile phone contacts) data associated with a device belonging to the subject, etc.

All or a portion of the input may be used by one or more of an image data NN 139a, an audial data NN 139b, and a physiological data NN 139c. For example, the image data obtained by camera 108, for example, may be analyzed by image data NN 139a to determine a first probability (or risk level) of whether the subject is exhibiting facial asymmetry. Further, the audial data may be received by audial NN 139b to determine a second probability (or risk level) of whether the user is exhibiting dysarthric speech. In addition, the physiological data may include blood pressure data that may be received by physiological NN 139c to determine a third probability (or risk level) of whether the user is exhibiting increased or high blood pressure compared to a prior measurement of blood pressure performed for the individual or compared to predefined blood pressure levels. In some embodiments, the image data may also be provided to physiological data NN 139c to perform additional physiological analysis based on image data. For example, additional physiological analysis may include image-based analysis of: a gait movement or pattern, a movement or pattern associated with a limb, a movement or pattern associated with a facial feature, etc.

The first probability (e.g., block 306), the second probability (e.g., block 310), and the third probability (e.g., block 314) may be provided to classifier analysis module 122 to be further analyzed in combination. The combined probabilities may be used to determine a risk level of the subject experiencing a stroke or stroke symptoms, or imminently experiencing one or more of the plurality of predefined stroke symptoms.

For example, the input 402, (e.g., biometric data including heart rate, blood pressure, and blood oxygen levels, image data (e.g., still images and/or video data) collected by mobile device 104 may be provided to ML models 142 and/or ML models 144, which may utilize algorithms 134 (e.g., NNs, ensemble learner(s), etc.) to determine the first, second, and/or third probabilities pertaining to stroke symptoms, as described throughout this disclosure. The probabilities may be provided to an ensemble learner to determine an overall risk of stroke and generate such risk(s) as output 404. The output 404 may trigger calls and/or text messages to device 104 and/or to one or more emergency contacts associated with device 104 if the risk is above one or more predefined thresholds associated with stroke risk and/or stroke symptoms. In some embodiments, the stroke prediction system 102 may trigger the device 104 to generate text messages and/or phone calls to the emergency contacts. In some embodiments, the stroke prediction system 102 may trigger the device 104 to automatically generate and send text messages and/or phone calls to the emergency contacts. In some embodiments, the stroke prediction system 102 may directly generate text messages and/or phone calls to the emergency contacts on behalf of the subject associated with mobile device 104. In general, an emergency contact may be defined by the subject in a contact list associated with the mobile device 104.

In operation, the classifier analysis module 122 may generate, analyze, and use classifiers 132 to determine output 404 representing stroke event and/or stroke symptom probabilities and/or stroke risk levels for a subject. The classifiers 132 may include logic for generating such output. For example, the classifiers 132 may include logic for generating or analyzing training data, training a model to detect stroke symptoms and/or events for a subject, performing key point detection on body or facial features, and/or classifying detected stroke symptoms and/or events according to the training data and/or rules (e.g., logic) programmed into the classifier.

For example, the classifiers 132 be used to employ a combination of: data augmentation (e.g., using an adversarial model), facial key point detection, and/or speech parsing. The classifiers may be used in combination with one or more of image data NN 139a, audial data NN 139b, and/or physiological data NN 139c to detect anomalies in the subject. Such anomalies may be used to determine a likelihood of the subject to be experiencing stroke events and/or stroke symptoms and thus an improvement in stroke detection technology. In particular, the image data NN 139a may use or generate one or more classifiers 132 to analyze input about the subject 101 including image data from device 104. Similarly, the audial data NN 139b may use or generate one or more classifiers 132 to analyze input about the subject 101 including audial data from device 104. In addition, the physiological data NN 139c may use or generate one or more classifiers 132 to analyze input about the subject 101 including physiological data from device 106 and/or image data from device 104, for example. In some embodiments, the system 100 may use a generative adversarial model to augment any or all of the received input data, as described elsewhere herein.

In general, the modified image data, audial data, and/or physiological data generated by the adversarial model may be used as training data 140 generated by system 102 and/or used or provided as additional training data from an external source. For example, output from any of the adversarial models described herein may be used to train a stroke detection model (e.g., ML model 142 and/or ML model 144) for use with the stroke prediction system 102. The stroke detection model may perform key point detection to pinpoint one or more salient facial features (e.g., eyes, nose, mouth, etc.) and may classify such features with one or more class labels using classifier analysis module 122 (e.g., using one or more classifiers 132). Example class labels may include, but are not limited to dysarthria, non-dysarthria, asymmetrical, normal, non-asymmetrical, stroke likely, stroke unlikely, etc.

Upon completion of classification and application of class labels, an output may be generated including a set of probabilities corresponding to each class label. The classifier analysis module 122 and/or system 100, and/or ensemble learning algorithms 134, in general, may determine which of the class labels indicates a highest probability. The determined class label having the highest probability (e.g., likelihood) may be generated as output 404 to indicate a stroke risk. In some embodiments, the output 404 may further indicate a likelihood of stroke event, a likelihood of the subject experiencing or imminently experiencing a stroke event and/or one or more stroke symptoms.

FIG. 5 illustrates a flow diagram of an example process 500 for predicting stroke symptoms for a subject (e.g., user). In general, the process 500 utilizes the systems 100, 102 and/or algorithms 134 described herein to obtain input pertaining to a subject and use the input to compute stroke risks and/or stroke probabilities for the subject. The probabilities may be used to trigger messaging, alerts, indicators, calls, etc., to inform the subject and/or one or more users about stroke-related symptoms and/or events pertaining to the subject.

At block 502, the process 500 may include receiving audial data representing one or more utterances of the subject. For example, the stroke prediction system 102 may receive one or more utterances of the subject 101 from mobile device 104 where microphone 110 captured the one or more utterances. In some embodiments, the sensor interface 116 may receive the audial data from mobile device 104 and provide the audial data to the stroke prediction system 102. In some embodiments, the mobile device 104 may directly send the audial data to the stroke prediction system 102.

At block 504, the process 500 may include receiving image data representing one or more images of at least a portion of a face of the subject. For example, the stroke prediction system 102 may receive one or more images of the subject 101 from mobile device 104 where one or more cameras 108 (e.g., a front facing camera) captured the facial images. The image data may be still images or video data. In some embodiments, the image data includes additional image data beyond images of a portion of the face such as still images and/or video images of: the face, an entire body, a portion of the body, or a gait or posture of the subject. In some embodiments, the sensor interface 116 may receive the image data from mobile device 104 and provide the image data to the stroke prediction system 102. In some embodiments, the mobile device 104 may directly send the image data to the stroke prediction system 102. In some embodiments, the subject may be accessing a video application or other visual application on the mobile device 104 while the camera 108 performs the image captures described herein.

At block 506, the process 500 may include receiving physiological data associated with the subject. For example, the stroke prediction system 102 may receive one or more inputs that represent physiological data associated with the subject 101. The wearable device 106 may use sensors 162, for example, to measure, characterize, or detect physical responses (e.g., stroke events, face or body movements (or lack thereof), facial expressions, heart rate, blood pressure data, blood oxygen data/levels, stress response, heat stroke, seizure, menopause, diabetes, calories expended, etc.) for a subject. In some embodiments, the sensor interface 116 may receive the image data from wearable device 106 and/or the mobile device 104 and provide the physiological data to the stroke prediction system 102. In some embodiments, the wearable device 106 and/or the mobile device 104 may directly send the physiological data to the stroke prediction system 102. The wearable device 106 may also be in communication with the mobile device 104 to exchange data and further exchange data with the stroke prediction system 102.

At block 508, the process 500 may include predicting, based on a plurality of predefined stroke symptoms and at least two of: the audial data, the image data, and the physiological data, a likelihood of the subject is experiencing or will imminently experience one or more of the plurality of predefined stroke symptoms. For example, the algorithms 134 may analyze two or more of: the audial data, the image data, and the physiological data to determine whether the subject is exhibiting a stroke event and/or stroke symptoms.

In some embodiments, the prediction may include accessing an ensemble learner (e.g., ensemble learning algorithms 134) that may provide the image data to a first ML model (e.g., that utilizes image data NN 139a) to generate analyzed image data for the subject 101. In some embodiments, the prediction may also include accessing the ensemble learner (e.g., ensemble learning algorithms 134) that may provide the audial data to a second ML model (e.g., that utilizes audial data NN 139b) to generate analyzed audial data for the subject 101. In some embodiments, the prediction may further include accessing the ensemble learner (e.g., ensemble learning algorithms 134) that may provide the physiological data to a third ML model (e.g., physiological data NN 139c) to generate analyzed physiological data for the subject. The stroke prediction system 102 may then generate, based on the analyzed image data, the analyzed audial data, and/or the analyzed physiological data, a classifier. The classifier may be programmed to execute instructions to generate an indication of the subject experiencing one or more of the plurality of predefined stroke symptoms, as described elsewhere herein. The system 102 may use the classifier to generate a likelihood of the subject experiencing a stroke event. The likelihood may include a notification of a symptom or event, a message or call indicating to seek help, a message or call indicating to seek out the subject or a way to locate the subject, medical instructions, etc. The likelihood may be provided as output to a mobile device (e.g., mobile device 104 and/or wearable device 106) associated with the subject or output to a device (e.g., mobile phone of a contact of the subject, email inbox, telephone, smart watch, etc.) associated with the one or more emergency contacts corresponding to the subject.

In some embodiments, the stroke prediction system 102 may use the generated classifier to generate a stroke risk score for the subject 101 indicating a level of risk of experiencing a stroke event. In some embodiments, the stroke prediction system 102 compiles one or more predictions into separate classifiers to be used to generate a stroke risk score for the subject 101 indicating a level of risk of experiencing a stroke event.

In some embodiments, the stroke prediction system 102 may generate, based on the analyzed image data, the analyzed audial data, and/or the analyzed physiological data, one or more classifiers that may be used to generate an indication that the subject 101 is currently experiencing one or more of the plurality of predefined stroke symptoms. The stroke prediction system 102 may use the classifier(s) to generate a likelihood of the subject experiencing a stroke event and/or to generate a stroke risk for the subject. The likelihood may be provided as output to the mobile device 104 and/or wearable device 106 that is associated with the subject 101, or another device associated with the one or more contacts corresponding to the subject.

At block 510, the process 500 may include causing generation of an alert for the subject and/or an alert for one or more emergency contacts corresponding to the subject, in response to determining that the likelihood is above a threshold level associated with one or more of the plurality of predefined stroke symptoms. For example, the monitoring engine 118 may detect one or more events with event detector 120 and may trigger use of one or more of: algorithms 134, classifier analysis module 122, user interface generator 136, ML models 142, and/or ML models 144, and alert generator 124 to generate and send one or more alerts to the mobile device 104, the wearable device 106, or another device associated with a contact of the user.

In some embodiments, the prediction performed by stroke prediction system 102 may include accessing an ensemble learner (e.g., ensemble learning algorithms 134) that can be arranged to provide the image data to the optional ML model 144 (e.g., utilizing image data NN 139*a*). An output from the ML model 144 may be received by system 102. The output may be based on the provided image data and may include a risk level of the subject 101 experiencing facial asymmetry associated with experiencing a stroke. The stroke prediction system 102 may generate, based on the risk level, the predicted likelihood as output to a mobile device 104 associated with the subject 101 or output to another device associated with the one or more emergency contacts corresponding to the subject 101.

In some embodiments, the prediction performed by stroke prediction system 102 may include accessing the ensemble learner (e.g., ensemble learning algorithms 134), which may provide the audial data, the image data, and/or the physiological data to a ML model 142 and/or machine model 144 to generate one or more predictions associated with stroke for the subject 101. The stroke prediction system 102 may receive from the ML model and based on the provided audial data, the image data, and the physiological data, a risk level of the subject 101 experiencing a stroke or imminently experiencing one or more of the plurality of predefined stroke symptoms.

In some embodiments, the process 500 further includes analyzing one or more inputs including one or more of: the audial data to determine whether the audial data exhibits speech dysarthria, the image data to determine whether the image data exhibits facial asymmetry, and/or the physiological data to determine whether the physiological data indicates a blood pressure above a predefined blood pressure level. The analysis may be performed by one or more algorithms 134 to perform preprocessing or pre-analysis before determining whether to provide the input to ML models/ensemble learning devices. If the preprocessing indicates that one or more events or symptoms are of concern for the health of the subject 101, the stroke prediction system may provide the input directly and/or may provide the analyzed one or more of the audial data, the image data, and the physiological data to an ensemble learner that may use the input/analyzed data to generate a stroke risk for the subject 101, as described elsewhere herein. The stroke prediction system 102 may receive the generated stroke risk at the mobile device 104 associated with the subject and associated with capture of one or more of the audial data, the image data, and/or the physiological data. In response to determining that the generated stroke risk is above a predefined stroke threshold, the stroke prediction system 102 may cause the mobile device 104 to execute a call or execute and send a text message to an emergency contact from a contact list on the mobile device. In this example, the audial data may include one or more utterances captured in near real time by the microphone 110 of the mobile device 104 associated with the subject 101. The image data may include still images or video data representing at least a portion of a face of the subject captured in near real time by the mobile device 104, for example. The physiological data may include blood pressure data or blood oxygen data for the subject 101. The physiological data may be captured by the wearable device 106 in communication with the mobile device 104. In such examples, the wearable device 106 may be a smart watch having sensors 162 including at least a blood pressure monitoring device for monitoring blood pressure for the subject 101.

The systems and methods of the implementations described herein and/or variations thereof can be embodied and/or implemented at least in part as a machine configured to receive a computer-readable medium (or computer program product) storing computer-readable instruction. The instructions are executed by computer-executable components integrated with the system and one or more portions of the hardware processor on the mobile device 104, the wearable device 106 and/or other communicatively coupled computing device. The computer-readable medium (or computer program product) can be stored on any suitable computer-readable media (e.g., memory 152) such as RAMs, ROMs, flash memory, EEPROMs, optical devices (e.g., CD or DVD), hard drives, floppy drives, or any suitable device. The computer-executable component can be a general or application-specific hardware processor, but any suitable dedicated hardware or hardware/firmware combination can alternatively or additionally execute the instructions.

A computer program product can be tangibly embodied in an information carrier. The computer program product may also contain instructions that, when executed, perform one or more methods and/or computer-implemented methods described herein. The information carrier may be a computer- or machine-readable medium, such as the memory 152, or other storage associated with system 102, device 104, device 106, and/or system 100 and/or processors 150.

As used in the description and claims, the singular form "a", "an" and "the" include both singular and plural references unless the context clearly dictates otherwise. For example, the term "signal" may include, and is contemplated to include, a plurality of signals. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5 percent, 1 percent or 0.1 percent. All numerical ranges provided herein are inclusive of the stated start and end numbers. The term "substantially" indicates mostly (i.e., greater than 50%) or essentially all of a device, substance, or composition.

The term "horizontal" as used herein is defined as a plane parallel to the conventional plane or surface of a heating element (e.g., heat source 410), regardless of its orientation. The term "vertical" refers to a direction perpendicular to the horizontal as just defined. Terms, such as "on", "above", "below", "bottom", "top", "side" (as in "sidewall"), "higher", "lower", "over", and "under", are defined with respect to the horizontal plane.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Implementations defined by each of these transitional terms are within the scope of this disclosure.

The examples and illustrations included herein show, by way of illustration and not of limitation, specific implementations in which the subject matter may be practiced. Other implementations may be utilized and derived therefrom, such that structural and logical substitutions and changes may be made without departing from the scope of this disclosure. Such implementations of the inventive subject matter may be referred to herein individually or collectively by the term "invention" merely for convenience and without intending to voluntarily limit the scope of this application to any single invention or inventive concept, if more than one is in fact disclosed. Thus, although specific implementations have been illustrated and described herein, any arrangement calculated to achieve the same purpose may be substituted for the specific implementations shown. This disclosure is intended to cover any and all adaptations or variations of various implementations. Combinations of the above implementations, and other implementations not specifically described herein, will be apparent to those of skill in the art upon reviewing the above description.

What is claimed is:

1. A computer-implemented method for predicting stroke symptoms for a subject, the method comprising:

receiving audial data representing one or more utterances of the subject;

receiving image data representing one or more images of at least a portion of a face of the subject;

receiving physiological data associated with the subject;

analyzing the audial data, the image data, and the physiological data;

generating, based on the analyzing, a classifier configured to generate an indication of the subject experiencing one or more of a plurality of predefined stroke symptoms, wherein the classifier is trained based on an augmented version of the audial data, wherein the augmented version of the audial data is generated by analyzing the one or more audial utterances, determining typical patterns of speech in the one or more audial utterances, and applying a change to the one or more utterances to emulate one or more audial stroke symptoms for the subject;

predicting, using the classifier, a likelihood that the subject is experiencing or will imminently experience one or more of the plurality of predefined stroke symptoms; and in response to determining that the likelihood is above a threshold level associated with one or more of the plurality of predefined stroke symptoms, causing generation of an alert for the subject and for one or more emergency contacts corresponding to the subject and providing the alert to a mobile device associated with the subject and a device associated with the one or more emergency contacts corresponding to the subject.

2. The computer-implemented method of claim 1, wherein generating the classifier comprises accessing an ensemble learner configured to:

augment the image data using a generative adversarial model to depict facial arrangement associated with stroke symptoms, wherein the augmenting comprises analyzing facial features to determine locations of the features, and applying a change to the features to approximate an image of a change in one or more facial features of the subject to emulate one or more stroke symptoms;

provide the augmented image data to a first machine learning model to generate analyzed image data for the subject;

provide the audial data to a second machine learning model to generate analyzed audial data for the subject; and provide the physiological data to a third machine learning model to generate analyzed physiological data for the subject.

3. The computer-implemented method of claim 1, wherein the prediction comprises accessing an ensemble learner configured to:

provide the image data to a machine learning model;

receive, from the machine learning model and based on the provided image data, a risk level of the subject experiencing facial asymmetry associated with experiencing a stroke; and generate, based on the risk level, the predicted likelihood as output to the mobile device associated with the subject or the device associated with the one or more emergency contacts corresponding to the subject.

4. The computer-implemented method of claim 3, wherein the image data comprises still images or video data representing at least a portion of the face of the subject captured by the mobile device associated with the subject.

5. The computer-implemented method of claim 3, wherein the image data is captured by a front facing camera of the device associated with the subject, the front facing camera capturing the image data during access of a video application on the mobile device associated with the subject.

6. The computer-implemented method of claim 1, wherein the physiological data comprises blood pressure data or blood oxygen data for the subject, the physiological data being captured by a wearable device in communication with a mobile device associated with the subject.

7. The computer-implemented method of claim 1, wherein the prediction comprises accessing an ensemble learner configured to:

provide the audial data, the image data, and the physiological data to a machine learning model; and receive, from the machine learning model and based on the provided audial data, the image data, and the physiological data, a risk level of the subject experiencing a stroke or imminently experiencing one or more of the plurality of predefined stroke symptoms.

8. The computer-implemented method of claim 1, further comprising analyzing one or more of:

the audial data to determine whether the audial data exhibits speech dysarthria;

the image data to determine whether the image data exhibits facial asymmetry; and the physiological data to determine whether the physiological data indicates a blood pressure above a predefined blood pressure level.

9. The computer-implemented method of claim 8, further comprising:

providing the analyzed one or more of the audial data, the image data, and the physiological data to an ensemble learner configured to generate a stroke risk for the subject;

receiving the generated stroke risk at a mobile device associated with the subject and associated with capture of one or more of the audial data, the image data, and the physiological data; and in response to determining that the generated stroke risk is above a predefined stroke threshold, causing the mobile device to execute a call or generate and send a text to an emergency contact from a contact list configured on the mobile device.

10. The computer-implemented method of claim 8, wherein:

the audial data comprises one or more utterances captured in near real time by a microphone of a mobile device associated with the subject;

the image data comprises still images or video data representing at least a portion of a face of the subject captured in near real time by the mobile device; and the physiological data comprises blood pressure data or blood oxygen data for the subject that is captured by a wearable device in communication with the mobile device.

11. The computer-implemented method of claim 1, wherein the alert comprises a text message sent to the one or more emergency contacts and a phone call placed to the one or more emergency contacts on behalf of the subject.

12. The computer-implemented method of claim 1, wherein the alert is additionally sent to emergency medical services system, the alert further comprising at least one of:

a notification of a symptom or event, a notification indicating to seek out the subject or a way to locate the subject, and a notification including medical instructions.

13. A system for predicting stroke symptoms for a subject, the system comprising:

at least one processor; and memory storing instructions that, when executed by the at least one processor, cause the system to execute instructions comprising:

receiving audial data representing one or more utterances of the subject;

generating, based on analyzing the received audial data, a classifier configured to generate an indication of the subject experiencing one or more of a plurality of predefined stroke symptoms, wherein the classifier is trained based on an augmented version of the audial data, wherein the augmented version of the audial data is generated by analyzing the one or more audial utterances, determining typical patterns of speech in the one or more audial utterances, and applying a change to the one or more utterances to emulate one or more audial stroke symptoms for the subject;

predicting, using the classifier a likelihood that the subject is experiencing or will imminently experience one or more of the plurality of predefined stroke symptoms; and in response to determining that the likelihood is above a threshold level associated with one or more of the plurality of predefined stroke symptoms, causing generation of an alert for the subject and for one or more emergency contacts corresponding to the subject, and providing the alert to a mobile device associated with the subject and to a device associated with the one or more emergency contacts corresponding to the subject.

14. The system of claim 13, wherein generating the classifier comprises accessing an ensemble learner configured to:

receive image data representing one or more images of at least a portion of a face of the subject;

receive physiological data associated with the subject;

augment the image data using a generative adversarial model to depict facial arrangement associated with stroke symptoms, wherein the augmenting comprises analyzing facial features to determine locations of the features, and applying a change to the features to approximate an image of a change in one or more facial features of the subject to emulate one or more stroke symptoms;

provide the augmented image data to a first machine learning model to generate analyzed image data for the subject;

provide the audial data to a second machine learning model to generate analyzed audial data for the subject; and provide the physiological data to a third machine learning model to generate analyzed physiological data for the subject.

15. The system of claim 14, wherein the prediction comprises accessing an ensemble learner configured to:

provide the image data to a machine learning model;

receive, from the machine learning model and based on the provided image data, a risk level of the subject experiencing facial asymmetry associated with experiencing a stroke; and generate, based on the risk level, the predicted likelihood as output to the mobile device associated with the subject or the device associated with the one or more emergency contacts corresponding to the subject.

16. The system of claim 15, wherein the image data comprises still images or video data representing at least a portion of the face of the subject captured by the mobile device associated with the subject.

17. The system of claim 14, wherein the physiological data comprises blood pressure data or blood oxygen data for the subject, the physiological data being captured by a wearable device in communication with the mobile device associated with the subject.

18. The system of claim 14, wherein the prediction comprises accessing an ensemble learner configured to:

provide the audial data, the image data, and the physiological data to a machine learning model; and receive, from the machine learning model and based on the provided audial data, the image data, and the physiological data, a risk level of the subject experiencing a stroke or imminently experiencing one or more of the plurality of predefined stroke symptoms.

19. The system of claim 14, wherein the instructions further comprise analyzing one or more of:

the audial data to determine whether the audial data exhibits speech dysarthria;

the image data to determine whether the image data exhibits facial asymmetry; and the physiological data to determine whether the physiological data indicates a blood pressure above a predefined blood pressure level.

20. The system of claim 19, wherein the instructions further comprise:

providing the analyzed one or more of the audial data, the image data, and the physiological data to an ensemble learner configured to generate a stroke risk for the subject;

receiving the generated stroke risk at the mobile device associated with the subject and associated with capture of one or more of the audial data, the image data, and the physiological data; and in response to determining that the generated stroke risk is above a predefined stroke threshold, causing the mobile device to execute a call or generate and send a text to an emergency contact from a contact list configured on the mobile device.

21. The system of claim 19, wherein:

the audial data comprises one or more utterances captured in near real time by a microphone of the mobile device associated with the subject;

the image data comprises still images or video data representing at least a portion of a face of the subject captured in near real time by the mobile device; and the physiological data comprises blood pressure data or blood oxygen data for the subject that is captured by a wearable device in communication with the mobile device.

22. A non-transitory computer-readable storage medium storing instructions that, when executed by at least one processor, cause the at least one processor to predict stroke symptoms for a subject by executing instructions comprising:

receiving audial data representing one or more utterances of the subject;

receiving image data representing one or more images of at least a portion of a face of the subject;

analyzing the audial data and the image data;

generating, based on the analyzing, a classifier configured to generate an indication of the subject experiencing one or more of a plurality of predefined stroke symptoms, wherein the classifier is trained based on an augmented version of the audial data, wherein the augmented version of the audial data is generated by analyzing the one or more audial utterances, determining typical patterns of speech in the one or more audial utterances, and applying a change to the one or more utterances to emulate one or more audial stroke symptoms for the subject;

predicting, based on a plurality of predefined stroke symptoms and at least two of: the audial data and the image data, a likelihood that the subject is experiencing or will imminently experience one or more of the plurality of predefined stroke symptoms; and in response to determining that the likelihood is above a threshold level associated with one or more of the plurality of predefined stroke symptoms, causing generation of an alert for the subject and for one or more emergency contacts corresponding to the subject, and providing the alert to a mobile device associated with the subject and to a device associated with the one or more emergency contacts corresponding to the subject.

23. The non-transitory computer-readable storage medium of claim 22, further comprising receiving physiological data for the subject, wherein generating the classifier comprises accessing an ensemble learner configured to:

augment the image data using a generative adversarial model to depict facial arrangement associated with stroke symptoms, wherein the augmenting comprises analyzing facial features to determine locations of the features, and applying a change to the features to approximate an image of a change in one or more facial features of the subject to emulate one or more stroke symptoms;

provide the augmented image data to a first machine learning model to generate analyzed image data for the subject;

provide the audial data to a second machine learning model to generate analyzed audial data for the subject; and provide the physiological data to a third machine learning model to generate analyzed physiological data for the subject.

24. The non-transitory computer-readable storage medium of claim 23, wherein the image data is captured by a front facing camera of the mobile device associated with the subject, the front facing camera capturing the image data during access of a video application on the mobile device associated with the subject.

25. The non-transitory computer-readable storage medium of claim 23, wherein the physiological data comprises blood pressure data or blood oxygen data for the subject, the physiological data being captured by a wearable device in communication with a device associated with the subject.

26. The non-transitory computer-readable storage medium of claim 23, wherein the prediction comprises accessing an ensemble learner configured to:

provide the audial data, the image data, and the physiological data to a machine learning model; and receive, from the machine learning model and based on the provided audial data, the image data, and the physiological data, a risk level of the subject experiencing a stroke or imminently experiencing one or more of the plurality of predefined stroke symptoms.

27. The non-transitory computer-readable storage medium of claim 23, wherein the instructions further comprise analyzing one or more of:

the audial data to determine whether the audial data exhibits speech dysarthria;

the image data to determine whether the image data exhibits facial asymmetry; and the physiological data to determine whether the physiological data indicates a blood pressure above a predefined blood pressure level.

28. The non-transitory computer-readable storage medium of claim 27, wherein the instructions further comprise:

providing the analyzed one or more of the audial data, the image data, and the physiological data to an ensemble learner configured to generate a stroke risk for the subject;

receiving the generated stroke risk at the mobile device associated with the subject and associated with capture of one or more of the audial data, the image data, and the physiological data; and in response to determining that the generated stroke risk is above a predefined stroke threshold, causing the mobile device to execute a call or generate and send a text to an emergency contact from a contact list configured on the mobile device.

29. The non-transitory computer-readable storage medium of claim 28, wherein:

the audial data comprises one or more utterances captured in near real time by a microphone of the mobile device associated with the subject;

the image data comprises still images or video data representing at least a portion of a face of the subject captured in near real time by the mobile device; and the physiological data comprises blood pressure data or blood oxygen data for the subject that is captured by a wearable device in communication with the mobile device.

30. The non-transitory computer-readable storage medium of claim 29, wherein the wearable device is a smart watch having a blood pressure monitoring device configured to monitor blood pressure for the subject.

* * * * *